United States Patent [19] [11] 4,404,230
Trummlitz et al. [45] Sep. 13, 1983

[54] 4-HYDROXY-1,2-BENZISOTHIAZOL-3(2H)-ONE-1,1-DIOXIDES AND SALTS THEREOF

[75] Inventors: Günter Trummlitz, Warthausen; Wolfgang Eberlein, Biberach; Wolfhard Engel, Biberach; Günther Schmidt, Biberach, all of Fed. Rep. of Germany

[73] Assignee: Dr. Karl Thomae GmbH, Biberach an der Riss, Fed. Rep. of Germany

[21] Appl. No.: 254,546

[22] Filed: Apr. 15, 1981

[30] Foreign Application Priority Data

Apr. 19, 1980 [DE] Fed. Rep. of Germany ....... 3015113

[51] Int. Cl.³ .................... C07D 275/06; A23L 1/236
[52] U.S. Cl. .................................. 426/548; 548/210; 548/211
[58] Field of Search ................. 426/548; 548/211, 210

[56] References Cited

U.S. PATENT DOCUMENTS 4,057,555 11/1977 Koike et al. .................. 548/210
4,140,697 2/1979 Batcho et al. .................. 426/548 X Primary Examiner—Joseph M. Golian
Attorney, Agent, or Firm—Hammond & Littell, Weissenberger and Muserlian

[57] ABSTRACT

Compounds of the formula

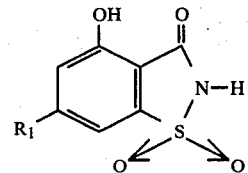

wherein $R_1$ is hydrogen or hydroxyl, and non-toxic, pharmacologically acceptable salts thereof formed with inorganic or organic bases. The compounds as well as their salts are useful as sweetening agents.

5 Claims, No Drawings

4-HYDROXY-1,2-BENZISOTHIAZOL-3(2H)-ONE-1,1-DIOXIDES AND SALTS THEREOF

This invention relates to novel 4-hydroxy-1,2-benzisothiazol-3(2H)-one-1,1-dioxides and non-toxic salts thereof, to methods of preparing these compounds, to sweetening compositions containing them, and to methods of using them as sweetening agents.

More particularly, the present invention relates to a novel class of compounds represented by the formula

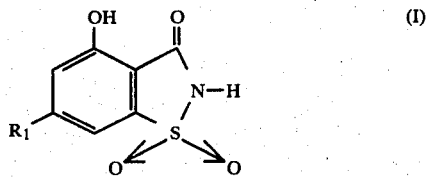

wherein $R_1$ is hydrogen or hydroxyl, and non-toxic, pharmacologically acceptable salts thereof formed with inorganic or organic bases.

The compounds embraced by formula I may be prepared by the following methods:

METHOD A

By alkaline hydrolysis of a 3-amino-1,2-benzthiazole-1,1-dioxide of the formula

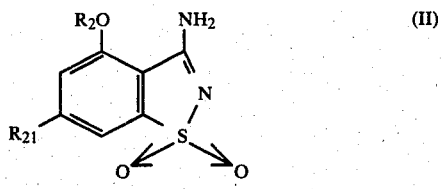

wherein
$R_2$ is hydrogen, alkyl or aralkyl, preferably alkyl of 1 to 6 carbon atoms, benzyl or phenethyl; and
$R_{21}$ is hydrogen, hydroxyl, alkoxy or aralkoxy, preferably alkoxy of 1 to 6 carbon atoms, benzyloxy or phenylethoxy.

When $R_2$ is hydrogen and $R_{21}$ is hydrogen or hydroxyl, the hydrolysis of the 3-amino compound II immediately forms the corresponding end product of the formula I or its salt. On the other hand, when $R_2$ is alkyl or aralkyl and/or $R_{21}$ is alkoxy or aralkoxy, the alkyl or aralkyl groups must subsequently be removed by ether cleavage to obtain the desired end product.

The hydrolysis of a compound of the formula II is carried out with a base. Thus, an aqueous solution of a compound of the formula II is treated with an inorganic base, for instance with an alkali metal hydroxide such as sodium hydroxide or potassium hydroxide, at temperatures between 50° C. and the boiling point of the solution. When $R_2$ in formula II is hydrogen or $R_{21}$ is hydroxyl, at least two equivalents of base are needed. However, when $R_2$ is hydrogen and $R_{21}$ is at the same time hydroxyl, at least three equivalents of base are required. In all other instances one equivalent of base or a small excess thereover is sufficient. After the hydrolysis has gone to completion the reaction mixture is acidified and, in the event that the product does not precipitate on its own, the aqueous solution is extracted with ethyl acetate for example.

The subsequent ether cleavage applied to a hydrolysis product which still has an alkoxy or aralkoxy substituent in the 4- and/or 6-position is effected by acid or alkaline methods. The acid method involves the use of Lewis acids such as boron halides, aluminum halides or pyridine hydrochloride. If a boron halide, such as boron tribromide or boron trichloride, is used, the reaction is carried out in an aprotic solvent, such as a halogenated hydrocarbon, at temperatures up to and including the boiling point of the reaction mixture. The boron halide is advantageously provided in molar excess. If an aluminum halide, such as anhydrous aluminum chloride, is used, carbon disulfide, nitrobenzene or toluene is advantageously employed as the aprotic solvent. The ether cleavage with pyridine hydrochloride is preferably performed without a solvent in the molten state.

The alkaline method is performed in a polar aprotic solvent; particularly suitable for this purpose is dimethylsulfoxide. This method involves the use of halides or pseudohalides which are provided in equimolar amounts or in 5- to 10-fold molar excess. The reaction temperature is in the range between 100° and 200° C., preferably between 150° and 180° C. Preferred halides are alkali metal halides, such as lithium iodide, lithium bromide, lithium chloride, sodium chloride, sodium bromide, sodium iodide, potassium chloride, potassium bromide or potassium iodide, but especially potassium bromide. Preferred pseudohalides are alkali metal pseudohalides, such as the corresponding cyanides and thiocyanates, but especially sodium cyanide, potassium cyanide or potassium thiocyanate.

METHOD B

By oxidation of an o-sulfamoyl-toluene of the formula

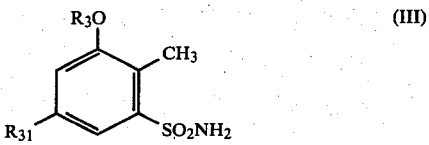

wherein
$R_3$ is alkyl or aralkyl, preferably alkyl of 1 to 6 carbon atoms, benzyl or phenethyl; and
$R_{31}$ is hydrogen, alkoxy or aralkoxy, preferably alkoxy of 1 to 6 carbon atoms, benzyloxy or phenylethoxy,
and subsequent cleavage of the phenol ether group.

Any conventional inorganic oxidizing agent, such as potassium permanganate, potassium chromate or potassium dichromate may be used. For example, the oxidizing composition may be an alkaline permanganate solution, such as a solution of potassium permanganate and sodium bicarbonate in water, or also a solution of potassium dichromate in an aqueous acid such as sulfuric acid.

The oxidation is carried out at temperatures between room temperature and the boiling point of the reaction mixture; for instance, when potassium permanganate is used, between 60° and 90° C.

The subsequent ether cleavage, that is, the removal of substituent $R_3$ and the removal of substituted $R_{31}$ if it is alkoxy or aralkoxy, is effected by the methods described in method A and yields the desired compound of the formula I.

METHOD C

By nucleophilic replacement of substituent $R_4$ in a 1,2-benzisothiazol-3(2H)-one-1,1-dioxide of the formula

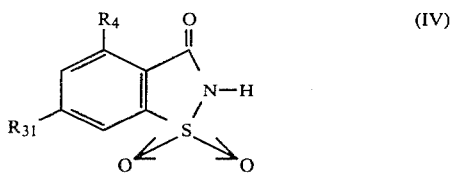

wherein $R_{31}$ has the meanings previously defined in connection with formula III, and $R_4$ is a nucleophilically replaceable leaving group, especially halogen, pseudohalogen or a diazonium cation, and, when $R_{31}$ is alkoxy or aralkoxy, subsequent cleavage of the phenol ether grouping.

While a compound of the formula I can be obtained from a corresponding 4-diazonium-substituted compound of the formula IV by simple heating to the boiling point of a solution thereof in water or in an aqueous acidic solution, for instance in dilute sulfuric acid, the exchange of a halogen or pseudohalogen substituent in the 4-position requires the presence of a catalyst. Examples of suitable catalysts are primarily copper powder, copper (I) or copper (II) salts in the presence of an alkali, for instance in the presence of sodium carbonate or potassium carbonate. Particularly preferred are mixtures of copper powder with copper salts, such as copper powder with copper (II) chloride. The exchange of a halogen or pseudohalogen substituent, such as a cyano or thiocyanate group, is effected in the presence of water at temperatures between 120° and 160° C.; the reaction is carried out in a pressure autoclave. After completion of the reaction the catalyst is removed from the reaction mixture by filtration, and the filtrate is concentrated by evaporation, acidified and extracted with ether, for example.

If a compound of the formula I in which $R_1$ is hydroxyl is to be prepared, the phenol ether grouping in the 6-position must be cleaved by the methods described in method A.

METHOD D

By cyclizing a 2-sulfamoyl-3-carboxylic acid derivative of the formula

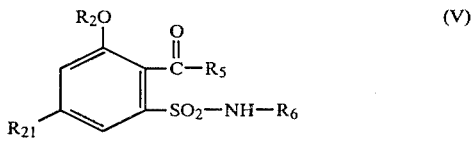

wherein $R_2$ and $R_{21}$ have the same meanings as in formula II;
$R_5$ is a nucleophilically exchangeable group, such as hydroxyl, alkoxy of 1 to 10 carbon atoms, phenoxy, naphthoxy, phenylalkoxy of 1 to 3 carbon atoms in the alkylene moiety, naphthylalkoxy of 1 to 3 carbon atoms in the alkylene moiety, or halogen; and
$R_6$ is hydrogen or tert. alkyl of 4 to 19 carbon atoms.

The cyclization is effected by treating the starting compound at temperatures between 0° and 100° C., preferably 50° to 70° C., with an acid such as phosphoric acid, polyphosphoric acid or sulfuric acid, or with a mixture of two or more of these acids. The end product formed thereby is isolated in conventional manner, for instance by addition of ice to the reaction mixture and purification of the precipitate formed thereby.

The cyclization may also be effected in the absence of a mineral acid by simply heating the starting compound to a temperature between 100° and 250° C. in the presence of a solvent such as o-dichloro-benzene or toluene, for example.

Basic reaction conditions, for instance cyclization in the presence of sodium methylate, have proved to be equally suitable.

When $R_2$ in the starting compound is alkyl or aralkyl or $R_{21}$ is alkoxy or aralkoxy, the cyclization product must subsequently be subjected to an ether cleavage reaction in order to obtain the desired compound of the formula I. The ether cleavage reaction is carried out in accordance with the methods described under method A.

The starting compounds of the formula II may be obtained by refluxing a 2-nitro-6-alkoxy- (or 6-aralkoxy-) benzonitrile, optionally substituted in the 4-position by an alkoxy or aralkoxy group, with tin and hydrochloric acid in the presence of tin(II)-chloride to form the corresponding 2-amino-6-alkoxy- (or 6-aralkoxy-) benzonitrile, optionally substituted in the 4-position by an alkoxy or aralkoxy group, and subsequently diazotizing this compound in the presence of glacial acetic acid and hydrochloric acid with sodium nitrite. At 20° C. the reaction mixture is introduced into a solution of sulfur dioxide in glacial acetic acid, and an aqueous solution of copper(II)-chloride is slowly added dropwise. A sulfochloride is obtained, which is dissolved in dioxane, and the solution is admixed with ethanol and concentrated aqueous ammonia. Cyclization into the corresponding 3-amino-4-alkoxy- (or 4-aralkoxy-) 1,2-benzoisothiazole-1,1-dioxide, optionally substituted in 4-position with an alkoxy or aralkoxy group, is completed by heating to 40° C. If in the last step an alkali metal halide or alkali metal pseudohalide such as potassium cyanide, e.g. in dimethylsulfoxide, is added, 3-amino-4-hydroxy-1,2-benzoisothiazole-1,1-dioxide or 3-amino-4,6-dihydroxy-1,2-benzoisothiazole-1,1-dioxide is directly obtained.

The starting compound of the formula III wherein $R_{31}$ is hydrogen may be obtained from the corresponding o-alkoxy (or o-aralkoxy-) o'-nitro-toluene by hydrogenating a solution of this compound in an alcohol, for example in ethanol, with Raney-nickel at 100 bar until the calculated amount of hydrogen is absorbed, whereby the corresponding 3-alkoxy- (or 3-aralkoxy-)-2-methylaniline is formed. The latter compound is subsequently dissolved in 50% acetic acid saturated with gaseous hydrogen chloride, and diazotized with sodium nitrite. The resulting diazonium salt solution is admixed with magnesium sulfate and subsequently poured into glacial acetic acid saturated with sulfur dioxide and containing some copper-(I)-chloride. After stirring for 4 hours at room temperature, water is added and the reaction mixture is extracted with methylene chloride. After removing the extraction agent, the extract is distilled in vacuo and the resulting pure sulfonic acid chloride, dissolved in ethanol, is admixed with concentrated aqueous ammonia. The corresponding 3-alkoxy or (3-aralkoxy-)-2-methyl-benzene sulfonamide of the formula III is formed thereby. The preparation of the starting compounds of the formula III wherein $R_{31}$ is alkoxy of aralkoxy is carried out analogously from the corresponding p-alkoxy (or p-aralkoxy-)-o-alkoxy (or -o-aralkoxy)-o'-nitro-toluenes.

The starting compounds of the formula IV may be obtained, for example, from 2-nitro-toluene substituted in 6-position by a nucleophilically exchangeable radical such as a chlorine atom, by hydrogenation with Raney-nickel in the presence of a solvent, such as ethanol. A 2-methylaniline correspondingly substituted in the 3-position is obtained thereby, which is subsequently diazotized in concentrated hydrochloric acid with sodium nitrite at $-7°$ to $-3°$ C. After filtering, the filtrate is poured in a thin stream into a suspension of copper(II)-chloride in a 30% solution of sulfur dioxide in glacial acetic acid. The temperature of the mixture rises to about 40° C. accompanied by a strong evolution of gas. After stirring for about 1 hour at 20° C. and for another hour at 35° C., the reaction mixture is admixed with ice. The resulting 2-methyl-benzene sulfonic acid chloride substituted in the 3-position is subsequently dissolved in dioxane and reacted with an ethanolic ammonia solution at temperatures between 50° C. and 80° C. to form the corresponding 2-methyl-benzene sulfonamide substituted in the 3-position. This sulfonamide is refluxed together with potassium carbonate and potassium permanganate in water for 1 hour. The reaction mixture is filtered while hot and the residue is washed with hot water. The combined filtrates are acidified with hydrochloric acid and cooled. 1,2-Benzoisothiazole-3(2H)-one-1,1-dioxide, substituted in the 4-position of the formula IV is obtained.

The starting compounds of the formula V may be prepared as follows: Diazotizing an m-alkoxy- (or aralkoxy-) aniline, dissolved in a polar solvent such as in glacial acetic acid, by adding hydrochloric acid and sodium nitrite. The reaction mixture is slowly poured into a mixture consisting of copper(II)-chloride, copper(I)-chloride and a 30% solution of sulfur dioxide in glacial acetic acid. The temperature rises to about 40° C. accompanied by heavy evolution of a gas, and the reaction mixture is maintained for 1 hour at this temperature. After diluting with ice water, the benzene sulfonic acid chloride substituted in 3-position is isolated from the organic phase, dissolved in tetrahydrofuran and reacted with tert. butylamine (about 7 hours at 60° C.). From the reaction mixture the corresponding N-tert. butyl-3-alkoxy- (or 3-aralkoxy-)-benzene sulfonamide is isolated. Other radicals $R_6$ may be prepared in analogy by reaction with other amines of the formula $R_6$—$NH_2$. The obtained benzene sulfonamide is subsequently dissolved in anhydrous tetrahydrofuran and reacted with lithium diisopropylamide or n-butyl-lithium at $-80°$ to $-50°$ C. After stirring for about 1 hour at 0° C., the reaction mixture is cooled to $-70°$ to $-50°$ C. and treated with carbon dioxide gas. At room temperature the reaction is allowed to go to completion, and from the reaction mixture a 2-(N-tert. butyl)-sulfamoyl-6-(alkoxy or aralkoxy)-benzoic acid of the formula V is isolated, where in this case $R_5$ is hydroxyl and $R_6$ is tert. butyl. Using other amines of the formula $R_6$—$NH_2$, the corresponding sulfamoyl benzoic acids substituted in 2-position are obtained. These benzoic acids may be esterified according to conventional methods.

The following examples illustrate the present invention and will enable others skilled in the art to understand it more completely. It should be understood, however, that the invention is not limited solely to the particular examples given below.

EXAMPLE 1

4-Hydroxy-1,2-benzoisothiazole-3(2H)-one-1,1-dioxide 5 gm (25.2 mmols) of 3-amino-4-hydroxy-1,2-benzoisothiazole-1,1-dioxide and 2.02 gm (50.5 mmols) of sodium hydroxide were refluxed in 15 ml of water for 6.5 hours. Subsequently, the solution was treated with activated charcoal at 60° C. and filtered. At 60° C. the filtrate was acidified with concentrated aqueous hydrochloric acid (about 5 ml, 0.06 mol). The resulting precipitate was filtered off, dried and recrystallized from water. 4.62 gm (92% of theory) of 4-hydroxy-1,2-benzoisothiazol-3(2H)-one-1,1-dioxide were obtained.

M.p.: 228° C.

IR ($CH_2Cl_2$): 3320 (NH, OH assoc.); 1720 (CO); 1335 and 1140 $cm^{-1}$ ($SO_2$).

MS: 199 (M+), 136, 119 and 108 m/e.

($C_7H_5NO_4S$ (199.19))—Calc.: C-42.20%; H-2.53%; N-7.03%; S-16.10%. Found: C-42.23%; H-2.60%; N-6.97%; S-16.10%.

The starting compound, 3-amino-4-hydroxy-1,2-benzoisothiazole-1,1-dioxide was prepared, starting from 2-nitro-6-methoxy-benzonitril (A. Russeland W. G. Tebbens, Org. Synthesis, Coll. Vol. III, page 293), in the following way.

2-Amino-6-methoxy-benzonitril 10 gm (56.1 mmols) of 2-nitro-6-methoxy-benzonitrile, 26.6 gm (220 mmols) of tin and 12.7 gm (56.1 mmols) of tin(II)-chloride were refluxed in 160 ml of semi-concentrated hydrochloric acid for 1.5 hours. After cooling the reaction mixture to 60° C., a solution of 40 gm of sodium hydroxide in 10 ml of water was added dropwise. After completion of the addition of sodium hydroxide solution (pH: about 4), the reaction mixture was adjusted to pH 9 with sodium carbonate, and the resulting precipitate was suction-filtered off. The filter cake was refluxed with 0.2 liter of ethanol for 20 minutes and filtered. The filtrate was evaporated, and 9 gm of crude product were obtained. Extraction of the tin hydroxide-product mixture was repeated and about 0.5 gm more of crude product was obtained.

The crude products from ethanol was recrystallized, using activated charcoal. By evaporation of the mother liquor a second fraction of the same purity was obtained. Yield: 7.5 gm (90% of theory) of 2-amino-6-methoxy-benzonitrile, m.p. 145° C.

3-Amino-B 4-methoxy-1,2-benzoisothiazole-1,1-dioxide 10 gm (67.5 mmols) of 2-amino-6-methoxy-benzonitrile were dissolved in 80 ml of glacial acetic acid at 60° C., and the solution was admixed with 80 ml of concentrated aqueous hydrochloric acid. The reaction mixture was cooled to $-5°$ C. and diazotized at this temperature by dropwise addition of a solution of 4 gm of sodium nitrite in 18.5 ml of water. After stirring for 30 minutes (the temperature rose to 0° C.), the reaction mixture was added in portions to a prepared mixture consisting of 94 ml of a 30% sulfur dioxide solution in glacial acetic acid and a solution of 1.7 gm of copper(II)-chloride in 4 ml of water. The temperature of the mixture was 20° C., and this temperature was also maintained during the diazonium salt solution introduction. Subsequently, the reaction mixture was stirred for 3 hours, whereby the color changed from red to yellowish-green and part of the sulfochloride separated out. The sulfo-chloride was filtered off, thoroughly washed with ice-water and dried (sulfochloride: 1st fraction). The filtrate was evaporated to a fourth of its volume and admixed with the 5-fold amount of ice water. The resulting sulfochloride crystals were filtered off, washed with ice-water and dried (2nd fraction). Both sulfochloride fractions were dissolved in 40 ml of dioxane and warmed to 40° C. At this temperature a mixture consisting of 20 ml of ethanol and 20 ml of concentrated aqueous ammonia was added dropwise, and the reaction mixture was stirred for 1 hour at 40° C. After refluxing for 2 hours, the reaction mixture was cooled and filtered off from the partial product (1st fraction), which was washed with water. The filtrate was evaporated in vacuo to dryness. The residue was suspended in water, filtered off and washed with water and a little cold ethanol (2nd fraction).

After drying, 10 gm (70% of theory) of 3-amino-4-methoxy-1,2-benzoisothiazole-1,1-dioxide were obtained.

M.p. 273°–276° C.

3-Amino-4-hydroxy-1,2-benzoisothiazole-1,1-dioxide

A mixture of 5 gm of 3-amino-4-methoxy-1,2-benzoisothiazole-1,1-dioxide and 1.63 gm of potassium cyanide in 15 ml of dimethyl-sulfoxide was heated to 130°–140° C. (bath temperature 160° C.) and kept at this temperature for 1.5 hours. After cooling, the reaction mixture was stirred into 250 ml of methylene chloride, and the resulting precipitate was filtered off, dried and dissolved in 30 ml of water. At 60° C. the solution was treated with charcoal and filtered while hot. The hot filtrate was adjusted to pH 1 with concentrated aqueous hydrochloric acid. After cooling, the resulting crystals were suction-filtered off, washed with a little ice water and dried in vacuo.

Yield: 43 gm (92% of theory) of 3-amino-4-hydroxy-1,2-benzoisothiazole-1,1-dioxide.

M.p.: 305° C. (decomp.)

EXAMPLE 2

4-Hydroxy-1,2-benzoisothiazol-3(2H)-one-1,1-dioxide-sodium salt 10 gm of 4-hydroxy-1,2-benzoisothiazol-3(2H)-one-1,1-dioxide were dissolved in isopropanol at 60° C. At this temperature the stoichiometric amount of sodium hydroxide solution (2.0 gm in 6 ml of water) was added. After cooling, the sodium salt of 4-hydroxy-1,2-benzoisothiazol-3(2H)-one-1,1-dioxide was filtered off, washed with isopropanol and ether and dried.

Yield: 10.8 gm (96% of theory).
M.p.: >350° C.
IR (KBr): 3320- (NH and OH assoc.), 1730 (CO), 1330 and 1140 cm$^{-1}$ (SO$_2$).
1H-NMR (DMSO-d$_6$): δ=10.6 (s, 1, OH, exchangeable with CD$_3$OD); 7.55 (dd, 1H, J=4 Hz, 6-H); 7.20 and 7.05 (two d, each 1H, J=4 Hz, 5-H and 7-H).

C$_7$H$_4$NNaO$_4$S×H$_2$O (239.19)—Calc.: C-35.15%; H-2.52%; N-5.85%; S-13.41%; Found: C-35.36%; H-2.40%; N-5.88%; S-13.45%.

EXAMPLE 3

4,6-Dihydroxy-1,2-benzoisothiazol-3(2H)-one-1,1-dioxide 1.5 gm (4.7 mmols) of 2-(N-tert. butyl)-sulfamoyl-4,6-dimethoxy-benzoic acid were added to 25 ml of polyphosphoric acid at 60° C., and the mixture was stirred for 1 hour at 80° C. The reaction mixture was poured over ice, and the resulting precipitate was filtered off. The filtrate was extracted three times with ethyl acetate, and the organic phase was dried and evaporated. The residue together with the previously obtained precipitate was recrystallized from methanol, yielding 0.74 gm (65% of theory) of 4,6-dimethoxy-1,2-benzoisothiazol-3(2H)-one-1,1-dioxide.

M.p.: 258° C.

C$_9$H$_9$NO$_5$S (243.25)—Calc.: C-44.44%; H-3.93%; N-5.76%; S-13.18%. Found: C-44.70%; H-3.75%; N-5.97%; S-13.32%.

The 4,6-dimethoxy derivative was taken up in 25 ml of ethylene chloride and admixed with 3.05 gm (12.2 mmols) of boron tribromide. After refluxing for 3 hours, another 3.05 gm of boron tribromide were added, and the reaction mixture was again refluxed for 3 hours. The reaction mixture was added to methanol and repeatedly evaporated to dryness after renewed addition of methanol. The residue was taken up in aqueous sodium bicarbonate solution. The solution was washed with ethyl acetate, acidified with hydrochloric acid and extracted with ethyl acetate. The extract was dried and evaporated. The residue, which was recrystallized from ethylene chloride, yielded 0.31 gm (48% of theory) of 4,6-dihydroxy-1,2-benzoisothiazol-3(2H)-one-1,1-dioxide.

M.P.: 286° C.

IR (KBr): 3420, 3260 (OH, NH), 1700 (CO), 1330 and 1145 cm$^{-1}$ (SO$_2$).

1H-NMR (CDCl$_3$+CD$_3$OD): δ=6.8 (d, 1H, J=1.5 Hz) and 6.57 (d, each 1H, J=1.5 Hz, 3-H and 5-H).

C$_7$H$_5$NO$_5$S (215.19)—Calc.: C-39.07%; H-2.34%; N-6.51%; S-14.90%. Found: C-39.15%; H-2.60%; N-6.58%; S-14.95%.

The starting compound, 2-(N-tert.butyl)-sulfamoyl-4,6-dimethoxy-1,2-benzoic acid, starting from 3,5-dimethoxyaniline, was prepared in the following way:

3,5-Dimethoxybenzene sulfonic acid chloride 50 ml of concentrated aqueous hydrochloric acid were added, while cooling (reaction temperature: max. +20° C.) to a solution of 26.6 gm (0.174 mol) of 3,5-dimethoxyaniline in 100 ml of glacial acetic acid. Over a period of 35 minutes a solution of 12 gm (0.174 mol) of sodium nitrite in 25 ml of water was added at −8° to −3° C. while cooling. After stirring for 1 hour on a cold bath, the reaction mixture was filtered, and the dark-brown filtrate was poured at 20°–25° C. into a stirred suspension of 10.2 gm (60 mmols) of copper (II)-chloride and 2 gm (20 mmols) of copper(I)-chloride in 120 ml of a 30% solution of sulfur dioxide in glacial acetic acid. The reaction temperature first rose to 40° C. and after it fell the reaction mixture was heated at 40° C. for another 90 minutes. After partial evaporation, the reaction mixture was poured into 2 liters of ice water. After three extractions with ether, the organic extracts were washed with water, sodium bicarbonate solution and again with water.

The ether phase was dried, treated with charcoal and evaporated.

Yield: 19.8 gm (48.5%) of 3,5-dimethoxy-benzene sulfonic acid chloride. A sample was purified by recrystallization from cyclohexane.

M.p.: 74° C.

N-tert. Butyl-3,5-dimethoxy-benzene sulfonamide

A solution of 7.3 gm (0.1 mol) of tert. butylamine in 20 ml of dioxane was added dropwise to a solution of 10.0 gm (42 mmols) of 3,5-dimethoxy-benzene sulfonic acid chloride in 100 ml dioxane at 40° C. over a period of 15 minutes. After the reaction temperature began to drop the reaction mixture was heated at 45° C. for 1.5 hours and at 60° C. for 2 hours. After cooling and filtering, the filtrate was evaporated in vacuo. The residue was recrystallized from cyclohexane.

Yield: 7.5 gm (64% of theory) of N-tert. butyl-3,5-dimethoxy-benzene sulfonamide.

M.p.: 140° C. (from ethanol)

$C_{12}H_{19}NO_4S$ (273.36)—Calc.: C-52.73%; H-7.01%; N-5.12%; S-11.73%. Found: C-53.00%; H-6.93%; N-5.05%; S-11.70%.

2-(N-tert. Butyl)-sulfamoyl-4,6-dimethoxy-benzoic acid 15.3 ml of a 15% solution of n-butyl-lithium in hexane (25 mmols) were added dropwise to a solution of 2.5 gm (25 mmols) of freshly distilled diisopropylamine in 40 ml of anhydrous tetrahydrofuran at $-10°$ to $-3°$ C. over a period of 10 minutes. After stirring for 20 minutes, the reaction mixture was cooled to $-70°$ C., and at this temperature a solution of 1.7 gm (6.2 mmols) of N-tert. butyl-3,5-dimethoxy-benzene sulfonamide in 50 ml of tetrahydrofuran was added dropwise thereto over a period of 40 minutes. After the addition was completed, the reaction mixture was allowed to stand until it cooled to room temperature and was then stirred for 1 hour.

After cooling to $-70°$ C. a stream of carbon dioxide was passed over the reaction mixture. When the reaction was finished, carbon dioxide was passed through the reaction mixture again, and the mixture thus obtained was allowed to warm to room temperature. The reaction mixture was evaporated in vacuo, and the solid residue was taken up in a mixture of water and ether. The organic phase was washed with water and evaporated, and 1.1 gm of the starting compound were obtained, which was again reacted. The aqueous phase was acidified with hydrochloric acid. The resulting precipitate was recrystallized from benzene, and 0.5 gm (86% yield, based on reacted starting material) of 2-(N-tert. butyl)-sulfamoyl-4,6-dimethoxy-benzoic acid were obtained.

M.p.: 209° C. (decomp.).

IR (KBr): 1730, 1710 (CO), 1320 and 1140 cm$^{-1}$ (SO$_2$)

1H-NMR (DMSO-d$_6$+CD$_3$OD): $\delta$=7.15 (d, 1H, J=1.5 Hz) and 6.90 (d, 1H, J=1.5 Hz, 3-H and 5-H); 4.05 (s, 3H) and 4.08 (s, 3H; 4-OCH$_3$ and 6-OCH$_3$); 1.18 (s, 9HC(CH$_3$)$_3$).

$C_{13}H_{19}NO_6S$ (317.37)—Calc. C-49.20%; H-6.04%; N-4.41%; S-10.10%. Found: C-48.96%; H-6.07%; N-4.35%; S-9.95%.

EXAMPLE 4

4-Hydroxy-1,2-benzoisothiazol-3(2H)-one-1,1-dioxide 2.5 gm (11.8 mmols) of 3-amino-4-methoxy-1,2-benzoisothiazole-1,1-dioxide were refluxed for 3 hours in a solution of 0.47 gm (11.8 mmols) of sodium hydroxide in 300 ml of water. The reaction mixture was filtered while still hot and acidified with hydrochloric acid. The resulting precipitate was filtered off, dried and recrystallized from benzene/ethyl acetate. 2.0 gm (9.4 mmols) of 4-methoxy-1,2-benzoisothiazol-3(2H)-one-1,1-dioxide (m.p.: 224° C.) were obtained, which were dissolved in 500 ml of ethylene chloride, and the solution was admixed with 10 gm (40 mmols) of boron tribromide. The reaction mixture was slowly heated and refluxed for 1 hour. The reaction mixture was evaporated in vacuo and then repeatedly evaporated in vacuo after addition of ethanol. The obtained product was recrystallized from water, yielding 1.6 gm (68% of theory) of 4-hydroxy-1,2-benzoisothiazol-3(2H)-one-1,1-dioxide.

M.p.: 228° C.

$C_7H_5NO_4S$ (199.19)—Calc.: C-42.20%; H-2.53%; N-7.03%; S-16.10%. Found: C-41.95%; H-2.50%; N-7.04%; S-16.08%.

EXAMPLE 5

4-Hydroxy-1,2-benzoisothiazol-3(2H)-one-1,1-dioxide 2.5 gm (11.8 mmols) of 3-amino-4-methoxy-1,2-benzoisothiazole-1,1-dioxide were reacted with sodium hydroxide analogous to Example 4. The reaction mixture was acidified, whereby 4-methoxy-1,2-benzoisothiazol-3(2H)-one-1,1-dioxide was obtained, which was subsequently heated at 200°-205° C. with 20 gm of pyridine hydrochloride. After cooling, the reaction mixture was extracted several times with boiling benzene, the residue was dissolved in water, and the aqueous solution was again extracted with boiling benzene. The combined benzene phases were dried and evaporated in vacuo. The residue was recrystallized from water, yielding 1.35 gm (57.5% of theory) of 4-hydroxy-1,2-benzoisothiazol-3(2H)-one-1,1-dioxide.

M.p.: 228° C.

$C_7H_5NO_4S$ (199.19)—Calc.: C-42.20%; H-2.53%; N-7.03%; S-16.10%. Found: C-41.90%; H-2.45%; N-7.18%; S-16.30%.

EXAMPLE 6

4-Hydroxy-1,2-benzoisothiazol-3(2H)-one-1,1-dioxide 2.5 gm (11.8 mmols) of 3-amino-4-methoxy-1,2-benzoisothiazole-1,1-dioxide were reacted with sodium hydroxide analogous to Example 5, and by subsequent acidification the reaction product was converted into 4-methoxy-1,2-benzoisothiazol-3(2H)-one-1,1-dioxide. The obtained compound, together with 650 mg (10 mmols) of potassium cyanide in dimethyl-sulfoxide, was heated at 180° C. for 3 hours. After addition of petroleum ether the potassium salt of the product was precipitated, and the precipitate was dissolved in water. After acidifying with aqueous hydrochloric acid, filtering and recrystallizing, 1.46 gm (62% of theory) of 4-hydroxy-1,2-benzoisothiazol-3(2H)-one-1,1-dioxide were obtained.

M.p.: 228° C. (from water).

$C_7H_5NO_4S$ (199.19)—Calc.: C-42.20%; H-2.53%; N-7.03%; S-16.10%. Found: C-42.18%; H-2.58%; N-7.06%; S-16.18%.

EXAMPLE 7

4-Hydroxy-1,2-benzoisothiazol-3(2H)-one-1,1-dioxide 2.5 gm (11.8 mmols) of 3-amino-4-methoxy-1,2-benzoisothiazole-1,1-dioxide were reacted analogous to Example 6. Instead of potassium cyanide, potassium bromide was used.

Yield: 1.05 gm (45% of theory) of 4-hydroxy-1,2-benzoisothiazol-3(2H)-one-1,1-dioxide M.p.: 228° C. (from water)

$C_7H_5NO_4S$ (199.19)— Calc.: C-42.20%; H-2.53%; N-7.03%; S-16.10%. Found: C-42.00%; H-2.61%; N-7.09%; S-16.21%.

EXAMPLE 8

4-Hydroxy-1,2-benzoisothiazol-3(2H)-one-1,1-dioxide 8.1 gm (40 mmols) of 3-methoxy-2-methyl-benzene sulfonamide and 5.5 gm (52 mmols) of anhydrous sodium carbonate were admixed with 300 ml of water, and a solution of 15.9 gm (500 mmols) of potassium permanganate in 400 ml of water was added dropwise at 70°-80° C. The reaction mixture was refluxed (about 1 to 2 hours) until decolorization and filtered while still hot. The filtrate was evaporated in vacuo to half its volume and acidified with concentrated aqueous hydrochloric acid. A small amount of the starting compound initially crystallized out and after standing overnight crystalline 4-methoxy-1,2-benzoisothiazol-3(2H)-one-1,1-dioxide could be filtered off.

A further quantity of the product could be obtained by extracting the aqueous mother liquor with ether. After recrystallization from benzene/ethyl acetate 4.8 gm (56% of theory) of 4-methoxy-1,2-benzoisothiazol-3(2H)-one-1,1-dioxide (m.p. 225° C.) were obtained. The obtained product was dissolved in 1000 ml of ethylene chloride, and the solution was admixed wiht 11.3 gm (45 mmols) of boron tribromide at $-10°$ C. Subsequently, the reaction mixture was stirred for 30 minutes at room temperature and refluxed for 1 hour. After evaporation in vacuo, the residue was heated for 15 minutes with 150 ml of 70% ethanol and then repeatedly evaporated in vacuo after addition of ethanol. Yield: 3.4 gm (75% of theory) of 4-hydroxy-1,2-benzoisothiazol-3(2H)-one-1,1-dioxide.

M.p.: 228° C. (from water).

$C_7H_5NO_4S$ (199.19)—Calc.: C-42.20%; H-2.53%; N-7.03%; S-16.10%. Found: C-42.10%; H-2.59%; N-7.06%; S-16.20%.

The starting compound was obtained from 2-methoxy-6-nitro-toluene in the following way:

3-Methoxy-2-methyl-aniline 200 gm (1.19 mols) of 2-methoxy-6-nitro-toluene were hydrogenated in 2.5 liters of ethanol in the presence of 25 gm of Raney nickel at 100 bar until the absorption of the calculated amount of hydrogen. The reaction mixture was filtered and evaporated in vacuo. After distillation 158.3 gm (97% of theory) of 3-methoxy-2-methylaniline were obtained.

B.p.: 126° C. at 16.25 mbar.

3-Methoxy-2-methyl-benzene sulfonamide 10.0 gm (73 mmols) of 3-methoxy-2-methyl-aniline were dissolved in 50 ml of aqueous 50% acetic acid which was saturated with gaseous hydrogen chloride, and the solution was diazotized with a solution of 5.5 gm (80 mmols) of sodium nitrite in 10 ml of water. A slight excess of nitrite was removed with urea. The resulting diazonium salt solution was admixed with 6 gm of magnesium sulfate and subsequently poured into 60 ml of glacial acetic acid saturated with sulfur dioxide and containing 3 gm of copper(I)-chloride.

The reaction mixture was slowly heated to room temperature and stirred for 4 hours. After addition of 500 ml of water, the crude product was extracted with methylene chloride. The organic phases were washed with water, with an aqueous sodium bicarbonate solution and again with water, dried and evaporated, and the residue was distilled in vacuo. The distillate obtained at a pressure of 19.5 mbar and at a boiling point of 110° to 135° C. (sulfonic acid chloride) was taken up in 50 ml of ethanol and admixed with concentrated aqueous ammonia. The reaction mixture was stirred for 15 minutes and evaporated in vacuo. The residue was recrystallized from methanol/water, yielding 4.6 gm (31% of theory) of 3-methoxy-2-methyl-benzene sulfonamide.

M.p.: 193° C.

EXAMPLE 9

4-Hydroxy-1,2-benzoisothiazol-3(2H)-one-1,1-dioxide

A mixture of 6.6 gm (30 mmols) of 4-chloro-1,2-benzoisothiazol-3(2H)-one-1,1-dioxide, 12.3 gm (90 mmols) of potassium carbonate, 0.6 gm of copper powder, 1.5 gm of copper (II) chloride and 110 ml of water was heated for 12 hours at 150° C. in a glass autoclave. The reaction mixture was then diluted with water, heated and filtered while hot. The filtrate was acidified with hydrochloric acid and extracted with ether. The ether extracts were evaporated, and the residue was recrystallized from water. Yield: 4.3 gm (72% of theory) of 4-hydroxy-1,2-benzoisothiazol-3(2H)-one-1,1-dioxide.

M.p.: 228° C.

$C_7H_5NO_4S$ (199.19)— Calc.: C-42.20%; H-2.53%; N-7.03%; S-16.10%. Found: C-42.10%; H-2.59%; N-7.06%; S-16.20%.

Starting from the 2-chloro-6-nitro toluene, the preparation of the starting compound, 4-chloro-1,2-benzoisothiazol-3(2H)-one-1,1-dioxide, was carried out by one of the following processes:

Process A

3-Chloro-2-methyl-aniline 100 gm (0.583 mol) of 2-chloro-6-nitro-toluene were hydrogenated in a suspension of 10 gm of Raney nickel in 1 liter of ethanol. When the calculated amount of hydrogen had been absorbed the reaction mixture was filtered, and the filtrate was evaporated in vacuo.

The residue was distilled in vacuo at 14 mbar. The compound obtained at 134°-140° C. was 3-chloro-2-methyl-aniline.

Yield: 72 gm (87% of theory).

B.p.: 140° C./14.3 mbar.

3-Chloro-2-methyl-benzene sulfonic acid chloride 30 gm (0.212 mol) of 3-chloro-2-methyl-aniline were admixed with 50 ml of concentrated aqueous hydrochloric acid. The reaction mixture was cooled to between $-7°$ and $-3°$ C. and at this temperature a solution of 14.6 gm (0.212 mol) of sodium nitrite in 50 ml of water was added dropwise thereto over a period of 1 hour. After stirring for a further hour at 0° C., 20.3 gm (0.1 mol) of magnesium chloride hexahydrate were added, and the reaction mixture was stirred for 10 minutes and then filtered. The filtrate was poured into a suspension of 12 gm (71 mmols) of copper (II)chloride in 250 ml of a 30% solution of sulfur dioxide in glacial acetic acid. During the addition the temperature of the reaction mixture rose from 20° C. to 40° C., accompanied by a strong evolution of gas. After stirring for 60 minutes at room temperature and for 60 minutes at 35° C., 500 gm of ice were added. The mixture was stirred until the ice had melted, and then filtered.

Yield: 38.2 gm (80% of theory) of 3-chloro-2-methyl-benzene-sulfonic acid chloride. The obtained product could be used directly in the subsequent reaction.

3-Chloro-2-methyl-benzene sulfonamide 38.2 gm (0.17 mol) of 3-chloro-2-methyl-benzene sulfonic acid chloride were dissolved in 200 ml of dioxane, and the solution was heated to 40° C. Over a period of 15 minutes a mixture of 100 ml of concentrated aqueous ammonia and 100 ml of ethanol was added dropwise thereto, whereby the temperature of the reaction mixture rose to 55° C.

Subsequently, the reaction mixture was heated at 70° C. for 2 hours, then cooled and filtered. (The filter cake consisted of 3,3′-dichloro-2,2′-dimethyl-diphenyl disulfide). The filtrate was evaporated in vacuo, and the residue was admixed with ice water. The precipitate formed thereby was suction-filtered off and washed with ice water. After recrystallization from ethanol/water 24 gm (69% of theory) of 3-chloro-2-methyl-benzene sulfonamide were obtained.

M.p.: 179° C.

$C_7H_8ClNO_2S$ (205.67)—Calc.: C-40.88%; H-3.92%; Cl-17.24%; N-6.81%; S-15.59%. Found: C-40.90%; H-3.85%; Cl-17.33%; N-6.71%; S-15.63%.

3-Chloro-2-methyl-benzene sulfinic acid was obtained by acidifying the filtrate with concentrated aqueous hydrochloric acid.

M.p.: 112° C.

Yield: 7.0 gm (22% of theory).

The sulfinic acid was converted with copper(II) chloride in formic acid into 3-chloro-2-methyl-benzene sulfonic acid chloride by heating for 1 hour at 40° C. and reacting with concentrated aqueous hydrochloric acid and ice.

Yield: 88%.

The sulfonic acid chloride was converted subsequently into 3-chloro-2-methyl-benzene sulfonamide.

Total yield: 85% of theory.

4-Chloro-1,2-benzoisothiazol-3(2H)one-1,1-dioxide

A mixture of 16.4 gm (80 mmols) of 3-chloro-2-methyl-benzene sulfonamide, 14 gm (100 mmols) of potassium carbonate, 33.2 gm (210 mmols) of potassium permanganate and 350 ml of water was refluxed for 1 hour. The reaction mixture was filtered while still hot, and the filter cake was washed with hot water. The combined filtrates were acidified with concentrated aqueous hydrochloric acid and cooled. The resulting crystals were suction-filtered off, washed with water and dried.

Yield: 12.6 gm (72.5% of theory) of 4-chloro-1,2-benzoisothiazol-3(2H)-one-1,1-dioxide.

M.p.: 210° C. (from water).

IR (KBr): 3420 (NH), 1730 (CO), 1330 and 1180 cm$^{-1}$ (SO$_2$).

$C_7H_4ClNO_3S$ (217.64)—Calc.: C-38.63%; H-1.85%; Cl-16.29%; N-6.44%; S-14.74%. Found: C-38.70%; H-1.80%; Cl-15.90%; N-6.70%; S-14.85%.

Process B

2-Chloro-6-nitro-benzoic acid

A mixture of 77.7 gm (0.453 mol) of 2-chloro-6-nitrotoluene, 190 gm (1.2 mol) of potassium permanganate, 500 ml of 1 N potassium hydroxide and 4 liters of water was heated for 8.5 hours at 100° C. After standing overnight, 25 gm (0.16 mol) of potassium permanganate were added, and the reaction mixture was heated for 2.5 hours more at 100° C. The unreacted starting material was distilled off by steam distillation. The remaining reaction solution was filtered, the filter cake was washed with hot water, and the combined filtrates were evaporated to about 750 ml. After acidifying with hydrochloric acid a precipitate was obtained, which was filtered off and dried.

Yield: 45.9 gm (50% of theory) of 2-chloro-6-nitro-benzoic acid.

M.p.: 166° C. (from ethylene chloride).

2-Chloro-6-nitro-benzoic acid chloride 1 ml of dimethyl formamide and 17.9 gm (0.15 mol) of thionyl chloride were added to a suspension of 20.1 gm (0.1 mol) of 2-chloro-6-nitro-benzoic acid in 150 ml of anhydrous benzene. The reaction mixture was stirred for 30 minutes and heated to reflux temperature. After 3 hours another 17.9 gm (0.15 mol) of thionyl chloride were added. The reaction mixture was further refluxed for 3 hours. After cooling, the reaction mixture filtered, and the filtrate was evaporated in vacuo.

Yield: 18.9 gm (85.9% of theory) of 2-chloro-6-nitro-benzoic acid chloride. The product obtained was an oil.

Methyl-2-chloro-6-nitro-benzoate 18.9 gm (86 mmols) of 2-chloro-6-nitro-benzoic acid chloride were added dropwise over a period of 10 minutes to 100 ml of methanol. The reaction mixture was refluxed for 4 hours and then evaporated in vacuo. The residue was treated with a little ice-cold methanol and filtered off.

Yield: 12.3 gm (66% of theory) of methyl-2-chloro-6-nitro-benzoate.

M.p.: 98° C. (from cyclohexane).

Methyl 6-chloro-anthranilate 4.5 gm (0.212 mol) of methyl 6-chloro-2-nitro-benzoate were hydrogenated with Raney nickel in 1.8 liters of methanol until the calculated amount of hydrogen was absorbed. The filtered reaction mixture was evaporated in vacuo, and the residue was distilled in vacuo.

Yield: 34.6 gm (88% of theory) of methyl 6-chloro-anthranilate.

B.p.: 158° C. at 14.3 mbar.

Methyl 6-chloro-2-chlorosulfonyl-benzoate 34.6 gm (0.186 mol) of methyl 6-chloro-anthranilate were added to 70 ml of concentrated aqueous hydrochloric acid while stirring and cooling. At 0° to +10° C. the reaction mixture was diazotized with a solution of 12.8 gm (0.186 mol) of sodium nitrite in 30 ml of water. After stirring at 0° C. for 45 minutes, the reaction mixture was poured into a stirred suspension of 2 gm of copper(I) chloride and 17 gm of copper (II)chloride in 160 ml of a 30% solution of sulfur dioxide in glacial acetic acid. After the evolution of nitrogen had ceased, the reaction mixture was stirred for 2 hours at room temperature. After extraction with ether, the organic extracts were washed, dried and evaporated.

Yield: 38.2 gm (76% of theory) of methyl 6-chloro-2-chlorosulfonyl-benzoate.

4-Chloro-1,2-benzoisothiazol-3(2H)-one-1,1-dioxide 150 ml of ethanol saturated with ammonia were added dropwise over a period of 30 minutes to a solution of 38.2 gm (0.141 mol) of methyl 6-chloro-2-chlorosulfonyl-benzoate in 150 ml of dioxane at 30°–50° C. Subsequently, the reaction mixture was heated for 2 hours at 40° C. and for 2 hours more at 60° C. After cooling, the reaction mixture was evaporated, treated with ether and filtered. The filter cake was boiled with water, filtered while hot, and the filtrate was acidified with hydrochloric acid. Yield: 19.8 gm (64.5% of theory) of 4-chloro-1,2-benzoisothiazol-3(2H)-one-1,1-dioxide.

M.p.: 210° C.

$C_7H_4ClNO_3S$ (217.64)—Calc.: C-38.63%; H-1.85%; Cl-16.29%; N-6.44%; S-14.73%. Found: C-38.65%; H-1.98%; Cl-16.20%; N-6.41%; S-14.75%.

EXAMPLE 10

4-Hydroxy-1,2-benzoisothiazol-3(2H)-one-1,1-dioxide 3.4 gm (12 mmols) of 2-(N-tert. butyl)-sulfamoyl-6-methoxy-benzoic acid were added over a period of 5 minutes to 50 gm of polyphosphoric acid. Subsequently, the reaction mixture was heated for 20 minutes at 70° C., and then ice was added thereto. The resulting precipitate was filtered off and recrystallized from water (1.6 gm; m.p. 224° C.; $C_8H_7NO_4S$: 4-methoxy-1,2-benzoisothiazol-3(2H)-one-1,1-dioxide).

The crystals were reacted with 24 ml (25 mmols) of boron tribromide in 400 ml of ethylene chloride for 1 hour at room temperature and for 2 hours at reflux temperature. Subsequently, the reaction mixture was evaporated, and the residue was repeatedly admixed with methanol and evaporated. After recrystallization from isopropanol 1.4 gm (58% of theory) of 4-hydroxy-1,2-benzoisothiazol-3(2H)-one-1,1-dioxide were obtained.

M.p.: 224° C.

$C_7H_5NO_4S$ (199.19)—Calc.: C-42.20%; H-2.53%; N-7.09%; S-16.10%. Found: C-42.16%; H-2.57%; N-6.99%; S-16.01%.

Starting from the m-anisidine, the starting compound, 2-(N-tert.butyl)-sulfamoyl-6-methoxy-benzoic acid, was prepared in the following way:

3-Methoxy-benzene sulfonic acid chloride 61.6 gm (0.5 mol) of m-anisidine were dissolved in 50 ml of glacial acetic acid, and the solution was admixed dropwise with 110 ml of concentrated aqueous hydrochloric acid. The mixture was cooled to 0° C. and diazotized with a solution of 38 gm (0.551 mol) of sodium nitrite in 75 ml of water. After stirring for 10–15 minutes, the reaction mixture was poured slowly to a mixture of 24 gm (0.14 mol) of copper (II) chloride, 5 gm of copper(I)chloride, 300 ml of a 30% solution of sulfur dioxide in glacial acetic acid and 450 ml of benzene, whereby a strong evolution of gas and an increase in the temperature up to 40° C. was observed. As soon as the reaction temperature dropped, the mixture was heated for 1 hour at 40° C. After cooling, the reaction mixture was diluted with 2.5 liters of ice water, filtered and the organic phase was separated. The organic phase was washed with water and sodium bicarbonate solution and evaporated.

Yield: 84.5 gm (82% of theory) of 3-methoxy-benzene sulfonic acid chloride.

N.-tert. Butyl-3-methoxy-benzene sulfonamide 49.5 gm (0.24 mol) of 3-methoxy-benzene sulfonic acid chloride were dissolved in 50 ml of tetrahydrofuran, and the solution was added dropwise over a period of 25 minutes to a solution of 40 gm (0.55 mol) of tert. butylamine in 200 ml of tetrahydrofuran. After stirring for 1 hour at room temperature and for 7 hours at 60° C., the reaction mixture was filtered, and the filtrate was evaporated in vacuo. The residue was treated with cyclohexane, yielded 54.1 gm (92.6% of theory) of N-tert. butyl-3-methoxy-benzenesulfonamide.

M.p.: 100° C.

2-(N-tert. butyl)-sulfamoyl-6-methoxy-benzoic acid

A solution of 3.3 gm (14 mmols) of N-tert. butyl-3-methoxy-benzene sulfonamide in 70 ml of anhydrous tetrahydrofuran was admixed dropwise in an atmosphere of nitrogen with 19 ml of a 15% solution of n-butyl-lithium in hexane (31 mmols) at −60° to −50° C. over a period of 15 minutes. The reaction mixture was subsequently stirred for 1 hour at 0° C. and after renewed cooling to between −70° and −50° C. a stream of carbon dioxide was passed therethrough. The treatment with carbon dioxide was continued for 1 hour at room temperature after the exothermic reaction had ceased. The reaction mixture was evaporated in vacuo, and the residue was taken up in a mixture of ice water and ether. The aqueous phase was washed with ether and acidified with hydrochloric acid. The precipitate was filtered off, yielding 3.6 gm (87% of theory) of 2-(N-tert.butyl)-sulfamoyl-6-methoxy-benzoic acid.

EXAMPLE 11

4-Hydroxy-1,2-benzoisothiazol-3(2H)-one-1,1-dioxide

A solution of 1,2-benzoisothiazol-3(2H)-one-1,1-dioxide-4-diazonium chloride, which was prepared by diazotization of 1.98 gm (10 mmols) of 4-amino-1,2-benzoisothiazol-3(2H)-one-1,1-dioxide with sodium nitrite in dilute hydrochloric acid, was reacted with 150 ml of aqueous 10% sulfuric acid, and the reaction mixture was heated on a water bath until the evolution of nitrogen had ceased. After cooling, the reaction mixture was strongly acidified with concentrated aqueous hydrochloric acid and extracted with ether. The organic phase was evaporated, the residue was dissolved in a little sodium hydrochloride, filtered and again acidified with hydrochloric acid. The crystals formed were recrystallized from water, yielding 0.98 gm (40% of theory) of 4-hydroxy-1,2-benzoisothiazol-3(2H)-one-1,1-dioxide.

M.p.: 228° C.

$C_7H_5NO_4S$ (199.19)—Calc.: C-42.20%; H-2.53%; N-7.03%; S-16.10%. Found: C-42.14%; H-2.57%; N-7.09%; S-15.98%.

The starting compound, 1,2-benzoisothiazol-3(2H)-one-1,1-dioxide, was prepared by the following method:

2-Methyl-3-nitro-benzene sulfonamide 7.5 gm (49 mmols) of 2-amino-6-nitro-toluene were dissolved in a mixture of 27.5 gm of concentrated sulfuric acid and 250 ml of water, and the solution was diazotized with a solution of 3.75 gm (54 mmols) of sodium nitrite in 7.5 ml of water at 0° to 5° C. After 2 hours the reaction mixture was added in portions to a previously prepared mixture of 90 ml of a sulfur dioxide solution in glacial acetic acid and a solution of 1.5 gm of copper-(II)chloride in 4 ml of water at 20° C. The further treatment and the reaction with ammonia was carried out analogously to the method described for the preparation of 3-methoxy-2-methylbenzene sulfonamide (Example 8).

Yield: 8.2 gm (77% of theory) of 2-methyl-3-nitro-benzene-sulfonamide.

C$_7$H$_8$N$_2$O$_4$S (216.21)—Calc.: C-38.89%; H-3.73%; N-12.95%; S-14.83%. Found: C-38.67%; H-3.79%; N-12.72%; S-14.81%

4-Nitro-1,2-benzoisothiazol-3(2H)-one-1,1-dioxide 8.0 gm (37 mmols) of 2-methyl-3nitro-benzene sulfonamide were oxidized with potassium permanganate in water analogous to Example 8. After extraction with ether, evaporation and recrystallization from water 3.8 gm (45% of theory) of the nitro compound were obtained.

M.p.: 239° C.

4-Amino-1,2-benzoisothiazol-3(2H)-one-1,1-dioxide 3.0 gm (13 mmols) of 4-nitro-1,2-benzoisothiazol-3(2H)-one-1,1-dioxide were dissolved in 100 ml of ethanol. The solution was hydrogenated with hydrogen, using a palladium/animal charcoal catalyst. After filtration, evaporation and recrystallization from ethanol 2.3 gm (89.5% of theory) of the amino compound were obtained.

M.p.: 244°–245° C.

C$_7$H$_6$N$_2$O$_3$S (198.19)—Calc.: C-42.42%; H-3.05%; N-14.13%; S-16.18%. Found: C-42.31%; H-3.12%; N-14.01%; S-16.18%.

1,2-Benzoisothiazol-3(2H)-one-1,1-dioxide-4-diazonium chloride 1.98 gm (10 mmols) of 4-amino-1,2-benzoisothiazol-3(2H)-one-1,1-dioxide were dissolved by addition of a solution of sodium carbonate in water and reprecipitated with concentrated aqueous hydrochloric acid. At 0° to 5° C. a solution of 700 mgm of sodium nitrite in 3 ml of water was added dropwise to this suspension, and the reaction mixture was stirred for 2 hours at 5° C. The diazonium salt solution thus obtained was directly used for further reactions without isolation of the diazonium salt.

The compounds of the present invention, that is, those embraced by formula I above and water-soluble, non-toxic, pharmacologically acceptable salts thereof, have useful properties. More particularly, they exhibit sweetening properties and are therefore useful as dietetic sweetening agents.

Examples of water-soluble, non-toxic, pharmacologically acceptable salts are the ammonium salts; the alkali metal salts, such as the sodium or potassium salts, but especially the sodium salts; and the alkaline earth metal salts, such as the calcium salts.

In general, a dietetic sweetening agent is expected to meet the following requirements:

(a) As an addition to foodstuffs, it must be absolutely safe, that is, it must exhibit no toxic or pharmacological effects;

(b) It must have satisfactory taste properties, where those of saccharose are considered to be exemplary; thus, the sweetening agent must not have an objectionable concurrent or after taste, and the sweet taste must be immediately perceptable and disappear again rapidly; and (c) It must be sufficiently water-soluble, temperature-stable in hot beverages, and acid-stable in sour fruit juices.

None of the dietetic sweetening agents presently known comes up to the above-mentioned expectations. Thus, the use of cyclamate and saccharine as sweetening agents is not without objection, as some toxicological tests at higher dosages have shown. Sweetening agents with a dipeptide structure are not sufficiently temperature- and acid-stable, while oxathiazinone derivatives are not completely satisfactory from the point of view of taste. Higher molecular natural substances lack sufficient stability and, moreover, due to their long lasting after-taste they are usable only under certain conditions.

We have discovered that the 4-hydroxy-1,2-benzoisothiazol-3(2H)-one-1,1-dioxides of the formula I and their water-soluble, non-toxic, pharmacologically acceptable salts formed with inorganic or organic bases possess a sweetening power at least equal to that of the sweetening agents heretofore used, as well as satisfactory taste properties, that is, no objectionable concurrent or after taste. They are freely water-soluble and, moreover, temperature- and acid-stable. Furthermore, the compounds exhibit a lack of toxic and pharmacological effects, which makes the use of them absolutely safe.

The sweetening and other desirable properties of the compounds of the present invention were ascertained and compared to those of known dietetic sweetening agents by the methods described below, and the results of these tests for a few representative species of the invention (A, B and C) and the known compounds (X, Y and Z) are shown in the tables, where A = 4-hydroxy-1,2-benzoisothiazol-3(2H)-one-1,1-dioxide, B = 4-hydroxy-1,2-benzoisothiazol-3(2H)-one-1,1-dioxide sodium salt, C = 4,6-dihydroxy-1,2-benzoisothiazol-3(2H)-one-1,1-dioxoide, X = cyclamate, Y = saccharine, and Z = 6-hydroxy-1,2-benzoisothiazol-3(2H)-one-1,1-dioxide.

A. DETERMINATION OF THE SWEETENING PROPERTIES

1. Determination of the threshold concentration

Aqueous solutions having concentrations of 1:12,500, 1:25,000, 1:50,000, and 1:100,000 were prepared of test compounds A, B and C and of comparison compounds X, Y and Z, and each was evaluated at 5 taste testers according to the following scoring system: Very sweet (=3 points), medium sweet (=2 points), weakly sweet (=1 point), and not sweet (=0 point). The tests were carried out as described by H. G. Schutz and F. J. Pilgrim in Food Research 22, 206 (1957). The dilution perceptible as sweet was defined as having the concentration at which the average value of the evaluation points reached 1.0 or more.

The following table shows the results obtained.

TABLE I

| Test compound | Concentration | Average value of evaluation points | Dilution perceptible as sweet |
|---|---|---|---|
| Invention: | | | |
| A | 1:25000 | 2.4 | 1:50000 |
|  | 1:50000 | 1.0 |  |
|  | 1:100000 | 0.2 |  |
| B | 1:25000 | 2.6 | 1:50000 |
|  | 1:50000 | 1.2 |  |
|  | 1:100000 | 0.0 |  |
| C | 1:25000 | 1.8 | 1:50000 |
|  | 1:50000 | 1.0 |  |
|  | 1:100000 | 0.0 |  |
| Prior art: | | | |

TABLE I-continued

| Test compound | Concentration | Average value of evaluation points | Dilution perceptible as sweet |
|---|---|---|---|
| X | 1:12500 | 0.6 | >1:12500 |
|   | 1:25000 | 0.2 |   |
|   | 1:50000 | 0.0 |   |
| Y | 1:25000 | 2.4 | 1:50000 |
|   | 1:50000 | 1.2 |   |
|   | 1:100000 | 0.4 |   |
| Z | 1:25000 | 1.4 | 1:25000 |
|   | 1:50000 | 0.6 |   |
|   | 1:100000 | 0.0 |   |

2. Determination of the relative sweetening power in comparison to saccharose The relative sweetening power (often also defined as degree of sweetness) of sweetening agents in comparison with saccharose (cane sugar) varies considerably with concentration. Thus, at the usual concentrations (i.e. a 2–10% solution of saccharose) the relative sweetening power of saccharine varies from 200 to 700. Therefore, for the determination of the relative sweetening power of the test compounds a 3% aqueous solution of saccharose was always used for comparison.

The determination of the relative sweetening power was carried out according to the methods of R. Pauli (Chemiker-Zeitung 44, 744 (1920) and T. Paul (Chemiker-Zeitung 45, 38 (1921)). Each test solution was tested by 5 taste testers.

The results obtained are shown in the following table:

TABLE II

| Test compound | Relative sweetening power (Saccharose = 1) |
|---|---|
| Invention: |   |
| A | 210 |
| B | 210 |
| C | 180 |
| Prior art: |   |
| X | 45 |
| Z | 140 |

3. Determination of the taste quality

Besides the absolute sweetening power of a sweetening agent, the taste quality is of great importance. Thus, the sweetening power of saccharin and cyclamate is much better than that of the saccharose, but they do not have the taste quality of saccharose. Thus, the metallic, bitter after taste and the bitter concurrent taste of saccharine can easily be demonstrated in taste tests. Since one of the principal requirement of a sweetening agent is a taste which is equivalent to that if saccharose, a determination of the taste qualities was carried out:

The tests were performed in analogy to the method of DuBois, G. A. Crosby, R. A. Stephanson and R. E. Wingard Jr., J. Agric. Food Chem. 25, 763 (1977). The test compounds were used as aqueous solutions at a concentration which corresponds to an about 5% saccharose solution. As comparison compound saccharose was used. The tests were carried out under identical conditions. Only the characterization of the taste was evaluated, because the intensity was already determined in the preceding experiments. The following criteria were determined by each tester: Percentage sweet to percentage bitter to percentage another taste quality. Furthermore, the presence or absence of an after taste of the individual test compounds was determined. Each substance was tested twice with regard to five different determinations.

The results are given in the following table.

TABLE III

| Test compound | Concentration | Number of determinations | Percentage sweet | Percentage bitter | Percentage other | After taste |
|---|---|---|---|---|---|---|
| Invention: |   |   |   |   |   |   |
| A | 1:10000 | 10 | 94 | 2 | 4 | 3 |
| B | 1:10000 | 10 | 96 | 2 | 2 | 5 |
| C | 1:10000 | 10 | 86 | 3 | 11 | 8 |
| Prior art: |   |   |   |   |   |   |
| Y | 1:10000 | 10 | 72 | 21 | 7 | 80 |
| Z | 1:10000 | 10 | 81 | 7 | 12 | 29 |
| Saccharose | 1:20 | 10 | 98 | 0 | 2 | 4 |

From the table it can be seen that the ideal taste profile of saccharose is not even approached by comparison substances Y and Z. However, substances A to C are to a large extent free of after taste which is surprising for dietetic sweetening agents. Moreover, the purity of the taste (94–96%) for substances A and B and 86% for substance C is excellent for sweeteners.

4. Determination of water-solubility and the acid-stability

Further requirements of a sweetener are good water-solubility and stability in an acid medium. It was found that substance B is easily soluble in water (solubility >> 1 gm/10 ml of water).

For the stability test, substance B at a concentration of 1% was dissolved in 0.1 N hydrochloric acid and kept at room temperature for 27 days. No changes could be detected. The solid substance was furthermore tested in daylight and at 60° C. in the absence and in the presence of light for 4 weeks. No changes could be detected either.

B. TEST FOR POSSIBLE PHARMACOLOGICAL EFFECTS

Substance B was tested with regard to possible pharmacological and toxicological effects.

The individual tests and the results are briefly described below.

1. Sedative and stimulating effect

Effect on motility of mice

Method:

Eight female Chbb:NMRI-mice (SPF) having a body weight from 20 to 26 g were tested in light beam cages after oral administration of the test compound in a suspension of 1% tylose. 30, 90 and 150 minutes after administration of the test compound, their motility was measured for 5 minutes each; a control group received only the solvent (tylose:carboxymethyl cellulose). The change in motility, given in percent with regard to that of the control group, was determined.

Results:

TABLE 1

| | Motility of mice, contacts/animal ± SD | | | |
|---|---|---|---|---|
| | | Minutes after application | | |
| Treatment | N | 30–35 | 90–95 | 150–155 |
| Control | 8 | 90 ± 35 | 83 ± 22 | 68 ± 23 |
| Substance B |   |   |   |   |
| 200 mg/kg p.o. | 8 | 92 ± 21 | 84 ± 28 | 49 ± 17 |

TABLE 1-continued

| | | Motility of mice, contacts/animal ± SD | | |
|---|---|---|---|---|
| | | Minutes after application | | |
| Treatment | N | 30-35 | 90-95 | 150-155 |
| Substance B % motility | | 102 | 101 | 72 |

N = number of animals

Even at a high dosage level of 200 mg/kg p.o. substance B did not affect the motility of mice.

2. Sedative or stimulating effect

Effect on motility of rats

Method:

In analogy to the method described by Führer and Feldhofen (Arzneimittel-Forschung 11, 1027, 1961) substance B was tested on 6 female Chbb:THOM-rats (SPF) having a body weight of 160-190 gm, after administration of 100 mg/kg p.o. in a suspension of 1% tylose. The motility of the rats in cages was measured for 30 minutes one hour after administration of the test compound. A control group received only tylose. The change in motility given in percent with regard to that of the control group was determined.

Results:

TABLE 2

| | Motility of rats, contacts/animal ± SD | |
|---|---|---|
| | | Minutes after application |
| Treatment | N | 60-90 |
| Control | 6 | 208 ± 49 |
| Substance B 100 mg/kg p.o. | 6 | 235 ± 58 |
| Substance B % motility | | 113 |

N = number of animals

It was found that substance B does not affect the motility of the rats.

3. Muscle relaxing and/or ataxic effect

Effect on the ability of mice to hold themselves in rotating cylinders

Method:

In analogy to the method described by Young and Lewis [Science 105, 368 (1947)], 10 female Chbb:NMRI-mice (SPF) having a body weight of 20-26 gm were tested to determine whether they were able to hold themselves in rotating cylinders after oral administration of 400 mg/kg of substance in aqua dist. The measurements were carried out 30-60, 90-120, 210-240 and 270-300 minutes after administration.

Results:

TABLE 3

| | | Effect on the holding ability of mice | | | |
|---|---|---|---|---|---|
| | | Animals which fell out, min. after application | | | |
| Treatment | N | 30-60 | 90-120 | 210-240 | 270-300 |
| Substance B 400 mg/kg p.o. | 10 | 2 | 2 | 1 | 0 |

N = number of animals

Even at dosages of 400 mg/kg p.o. substance B does not affect the holding ability of mice. The substance shows no muscle relaxing or coordination inhibiting effect.

4. Barbiturate-potentiating effect

Effect on the duration of hexobarbital anesthesia in mice

Method:

According to Winter [Pharmacol. exp. Ther. 94, 7, (1948)], 100 mg/kg of substance B in a suspension of 1% tylose were administered perorally to 10 male Chbb:NMRI-mice (SPF) having a body weight of 20 to 26 gm. A control group received only the suspension agent. After 1 hour all animals were injected i.p. with 80 mg/kg of hexobarbital. The mice were put on a metal plate at 37° C. and the time from the beginning of the loss of the righting reflex until the recurrence of this reflex was measured as the duration of the anesthesia. This time difference was calculated in percent with regard to that of the control group.

Results:

TABLE 4

| Effect on the duration of hexobarbital anesthesia in mice | | |
|---|---|---|
| | Duration of anesthesia | |
| Treatment | minutes ∓ SD | % |
| Substance B 100 mg/kg p.o. | 15.65 ± 6.32 | 106 |
| Control | 14.70 ± 3.62 | 100 |

At dosages of 100 mg/kg p.o. in mice substance B does not show any effect on the duration of hexobarbital anesthesia.

5. Anticonvulsive effect

Effect on maximum electroshock convulsions in mice

Method:

According to Swinyard, Brown and Goodman [J. Pharmacol. exp. Ther. 106, 319 (1952)], 200 mg/kg of substance B in aqua dist. solution were administered perorally to 10 male Chbb:NMRI-mice (SPF). After 30, 150 and 300 minutes tonic extensor spasms were induced by alternating current via head-electrodes (50 mA, 50 Hz, 2 sec. duration). Tonic extensor spasms of the extremities cannot be observed after treatment with substances having an anticonvulsive activity.

Results:

TABLE 5

| Effect on maximum electroshock convulsions in mice. | | | | |
|---|---|---|---|---|
| | | Number of protected animals, minutes after administration | | |
| Treatment | N | 30 | 150 | 300 |
| Substance B 200 mg/kg p.o. | 10 | 0 | 0 | 0 |

N = number of animals

At a dosage of 200 mg/kg p.o. in mice substance B does not show any anticonvulsive activity.

6. Antidepressive effect

Effect on reserpine-hypothermia in mice

Method:

In analogy to Askew [Life Sci. 2, 275, (1963)] hypothermia was induced by s.c. administration of 3 mg/kg of reserpine in male Chbb:NMRI-mice (SPF) having a body weight of 20-26 gm. After 17 hours the lowered body temperature was measured, and substance B was administered orally to 10 animals at a dosage of 40 and 100 mg in aqua dist. solution. A control group received only the solvent p.o.; 1 to 4 hours after administration the temperature was measured every hour. The values given in the table are at average temperature values ±SD.

Results:

TABLE 6

Behaviour of body temperature in comparison with controls; °C. ± SD.

| Treatment | N | before admin. | hours after administration | | | |
|---|---|---|---|---|---|---|
| | | | 1 | 2 | 3 | 4 |
| Controls | 10 | 22.6 ± 0.2 | 24.6 ± 1.3 | 25.7 ± 1.9 | 26.2 ± 2.1 | 26.5 ± 1.9 |
| Substance B 400 mg/kg p.o. | 10 | 22.7 ± 0.3 | 24.0 ± 1.4 | 24.7 ± 1.7 | 25.3 ± 1.7 | 25.9 ± 1.4 |
| Substance B 100 mg/kg p.o. | 10 | 23.3 ± 0.5 | 26.0 ± 1.7 | 26.7 ± 1.4 | 26.6 ± 1.2 | 26.8 ± 1.4 |

N = number of animals

At dosages of 40 and 100 mg/kg p.o. substance B does not show an effect on hypothermia in mice induced by reserpine.

7. Antiexudative effect

Effect on the kaolin edema in rats

Method:

According to Hillebrecht [Arzneimittel-Forschung 4, 607 (1954)] an edema was induced in 20 Chbb:THOM-rats (SPF) of both sexes having a body weight of 125–150 gm by subplantar injection of 0.05 ml of a 10% kaolin suspension in the hind paw. 30 minutes before, 100 mg/kg of substance B as aqua dist. solution was orally administered to 10 animals. Ten control animals received only the solvent. The thickness of the paw was measured before the administration of the test compound and 5 hours after administration. The edema-altering effect was expressed in percent of the average degree of swelling of the control animals.

Results:

TABLE 7

Effect against the kaolin edema in rats.

| Treatment | N | Average degree of swelling | Inhibition in % |
|---|---|---|---|
| Substance B 100 mg/kg p.o. | 10 | 239.0 | 13.7 |
| Control | 10 | 277.0 | |

N = number of animals

At a dosage of 100 mg/kg p.o. substance B does not show any antiexudative effect in rats.

8. Ulcerogenic effect in rats

Method:

200 mg/kg of substance B in 1% tylose suspension were administered perorally to 10 male and female (1:1) Chbb:THOM-rats (SPF) having an approximate body weight of 200 gm. A control group received only the suspension agent. After 4 hours all animals were killed, the stomach was dissected and inspected with regard to lesions of the mucosa.

Results:

TABLE 8

Ulcerogenic effect in rats.

| Treatment | N | Animals having stomach lesions |
|---|---|---|
| Substance B 200 mg/kg p.o. | 10 | 0 |

TABLE 8-continued

Ulcerogenic effect in rats.

| Treatment | N | Animals having stomach lesions |
|---|---|---|
| Control | 10 | 0 |

N = number of animals.

At a dosage of 200 mg/kg p.o. substance B does not show any ulcerogenic effect in rats.

9. Effect on choleresis in rats

Method:

A cannula was tied to the ductus choledochus of anesthetized, fasted male Chbb:THOM-rats (SPF) having a body weight of 180–220 gm, and the rate of flow of bile liquid was registered via a drop counter. 100 or 200 mg/kg of substance B in aqua dist. solution were administered intraduodenally to each of 10 animals. A control group received only the solvent. The number of the drops received within 1 hour before the treatment was compared with the number of the drops received within 1–5 hours after treatment.

Results:

TABLE 9

Choleresis in rats, average number of drops/ hr ± SD

| Treatment | N | Value before treatment | Hours after treatment | | | | |
|---|---|---|---|---|---|---|---|
| | | | 1 | 2 | 3 | 4 | 5 |
| Control | 10 | 62.6 ±4.8 | 57.1 ±4.8 | 55.8 ±5.1 | 56.3 ±6.0 | 56.6 ±6.9 | 58.1 ±10.0 |
| Substance B 100 mg/kg i.d. | 10 | 55.1 ±9.1 | 53.3 ±10.1 | 51.7 ±9.2 | 50.7 ±9.3 | 49.9 ±9.2 | 49.5 ±9.1 |
| Substance B 200 mg/kg i.d. | 10 | 47.1 ±11.5 | 44.1 ±9.8 | 43.1 ±10.3 | 43.1 ±8.2 | 43.5 ±8.2 | 44.4 ±8.0 |

N = number of animals.

In Table 10 the average number of drops 1–5 hours after treatment is shown in percent, compared with the values before treatment.

TABLE 10

Choleresis in rats in %, compared with the values before treatment.

| Treatment | N | Value before treatment | Hours after treatment | | | | |
|---|---|---|---|---|---|---|---|
| | | | 1 | 2 | 3 | 4 | 5 |
| Control | 10 | 100 | 91 | 89 | 90 | 90 | 93 |
| Substance B 100 mg/kg i.d. | 10 | 100 | 97 | 94 | 92 | 91 | 90 |
| Substance B 200 mg/kg i.d. | 10 | 100 | 94 | 92 | 92 | 92 | 94 |

N = number of animals

As tables 9 and 10 show, at dosages of 100 and 200 mg/kg substance B does not show any intraduodenal effects on choleresis in rats.

Cardiovascular effects

Effect on the blood circulation in anesthetized cats

Method:

In 3 adult anesthetized cats the following parameters were measured:

The arterial blood pressure in the Arteria carotis by means of a Statham pressure transducer;

The heart rate by means of a Grass-tachograph;

The respiration rate by means of a Fleisch pneumotachograph;

10 mg/kg of substance B as a solution in aqua dist. were administered i.v.

Results:

TABLE 11

Blood pressure heart rate and respiration rate of anesthetized cats, change compared with values before the administration of the substance in %.

| Treatment | N | Change in % blood pressure | heart rate | respiration rate |
|---|---|---|---|---|
| Substance B 10 mg/kg i.v. | 3 | +1 | −1 | −2 |

N = number of animals.

At a dosage of 10 mg/kg i.v. substance B does not show any effect on the arterial blood pressure, the heart rate and the respiration rate in anesthetized cats.

11. Effect on thrombocyte aggregation

Method:

The thrombocyte aggregation was measured according to Born and Cross [J. Physiol. 170, 397 (1964)] in platelet-rich plasma obtained by centrifuging citrate blood. The change in the maximum aggregation rate in % compared with a control, and the percent change in the "optical density" were the measured parameters. The aggregation was induced by collagen.

Results:

TABLE 12

Effect on thrombocyte aggregation induced by collagen.

| Treatment | Change in % max. aggregation rate | optical density |
|---|---|---|
| Substance B $10^{-4}$ mol/liter | ±0 | ±0 |

At dosages of $1 \times 10^{-4}$ mol/liter substance B does not show any effect on thrombocyte aggregation induced by collagen.

12. Bacteriostasis and fungistasis

Methods:

Substance B was tested with regard to its bacteria- and fungi-inhibiting effect by the serial dilution test and agar diffusion test.

Results:

In the serial dilution test 320 μg/ml of substance B did not show any inhibiting effect on *Staphylococcus aureus* SG 511, *Streptococcus Aronson*, Sc. *pyogenes* ATCC 8688, *Escherichia coli* ATCC 9637, *Pseudomonas aeruginosa* Hbg., *Serratia marcescens* ATCC 13880, *Candida albicans* ATCC 10231, *Trychophyton mentagrophytes* ATCC 9129 and *Aspergillus niger*.

Also, in the agar diffusion test 16,000 μg/ml of substance B did not show any inhibiting effect on the same microorlganisms.

13. Diuretic effect

Effect on diuresis in rats

Method:

Male Chbb:THOM-rats (SPF) having a body weight of 180–210 gm were kept away from food with free access to water for 24 hours before the test. Substance B was administered orally at dosages of 50, 100 and 200 mg/kg in aqua dist. solution of the rate of 1 ml/100 gm body weight to 6 animals/dose. Additionally, 4 ml water/100 gm body weight were administered orally. A control group received only the solvent and the same additional amount of water.

Five hours after treatment, the excreted volume of urine of each group was measured, and the concentration of $Na^+$, $K^+$ and $Cl^-$ was determined photometrically and complexometrically.

Results:

TABLE 13

Diuresis in water-loaded rats

| Treatment | N | Microval/kg Na+ | K+ | Cl− | Urine ml/kg |
|---|---|---|---|---|---|
| Substance B | | | | | |
| 50 mg/kg p.o. | 6 | 456.6 | 456.6 | 616.4 | 45.7 |
| 100 mg/kg p.o. | 6 | 401.9 | 321.5 | 325.5 | 40.2 |
| 200 mg/kg p.o. | 6 | 467.6 | 425.1 | 535.7 | 42.5 |
| Control | 6 | 274.9 | 471.2 | 353.4 | 39.3 |

N = number of animals.

At dosages of 50, 100 and 200 mg/kg p.o. substance B does not show any effect on diuresis in rats. All values are within the confidence limit ($p \leq 0.05$) of average control values.

$Na^+$: 154.3–660.9 μVal/kg
$K^+$: 146.3–550.0 μVal/kg
$Cl^-$: 189.9–673.1 μval/kg
Volume: 37.1–49.3 ml/kg.

14. Mucosa compatibility

Local compatibility in the eye of the rabbit

Method:

Groups of 4 rabbits each of both sexes were given 1 drop of a 1% solution of substance B in aqua dist. into the conjunctival sack of the eye. 15, 30, 60, 90, 120 minutes as well as 24 hours after treatment the eyes of the rabbits were observed with regard to an irritation of the conjunctiva (redness, secretion etc.) as well as with regard to a change in the pupil. The second eye of each animal served as control.

Results:

TABLE 14

Local compatibility, eye of the rabbit.

| Treatment | N | Result |
|---|---|---|
| Substance B | | |
| 1% | 4 | No irritation of the conjunctiva, no change in the pupil. |
| 10% | 4 | No irritation of the conjunctiva, no change in the pupil. |

N = number of animals.

Substance B does not show any incompatibility when dropped into the eye of the rabbit.

C. TESTS FOR POSSIBLE ACUTE, SUBACUTE, TOXIC AND MUTAGENIC EFFECTS

1. Test for acute toxicity

The acute toxicity was determined after oral administration of substance B to male and female mice, rats and dogs. The substance was administered to mice and rats in the form of a suspension in tylose and to dogs in the form of a solution in water. The following table shows the number of the animals which died within 1, 7 and 14 days after treatment.

| Kind of animals | Dose | Number of animals | Animals which died within the observation time of | | |
|---|---|---|---|---|---|
| | | | 1 day | 7 days | 14 days |
| Mouse | 10 g/kg | 10 | 0 | 0 | 0 |
| Rat | 10 g/kg | 6 | 0 | 0 | 0 |
| Dog | 5 g/kg | 2 | 0 | 0 | 0 |

During the observation time no animals died. Moreover, no toxic symptoms could be observed. All animals survived and showed completely normal behavior.

2. Test for subacute toxicity

The subacute toxicity of substance B was tested in rats and dogs.

Test in the rat:

The test was carried out on 10 male and 10 female Chbb:Thom-rats. During a period of 5 weeks 750 mg/kg of substance B were administered to the animals daily. During the test period the animals showed a normal behavior. No spontaneous deaths could be observed. After the 5 weeks the animals were killed, and the following organs were dissected for histological examination: heart, lungs, liver, spleen, suprarenals, brain, kidney and pancreas.

The histological examination of these organs did not show any pathological findings which could be connected with the administration of the test substance.

Test in the dog:

The test was carried out in each 3 male and 3 female beagles. Over a period of 5 weeks 750 mg/kg of substance B were administered orally. The animals did not show any abnormal behavior. Spontaneous deaths could not be observed.

After the test period of 5 weeks the animals were killed and the same organs as above were taken for histological examination.

No changes could be observed.

3. Test for mutagenic effects

The most important requisite for a sweetening agent is that it must be harmless to health. Most sweetening agents, however, do not meet this requirement. Thus, for example, saccharin shows a mutagenic effect [R. P. Batzinger, S.-Y.L. On and E. Buedign. Science 198, 944 (1977)], which puts its use as an absolutely safe sweetening agent in question.

Compound B was tested according to the AMES-system [Mutation Research 31, 347–364 (1975)] for mutagenic properties. In order to show the whole spectrum of induced molecular DNA-damage (base substitutions, frame-shift mutations, deletions) the auxotrophic bacterial strains *Salmonella typhimurium* TA 98, TA 100, TA 1535, TA 1537 and TA 1538 were used as genetic indicators.

The tests for all microorganisms were carried out such that the effect of the test compound on a microsomal enzyme system together with the corresponding co-factors could be tested, and furthermore to determine the effect on enzyme induction. The tests were performed without an activating system and in the presence of an activating system. For the in-vitro-activation S-9 supernatants (fractions of the endoplasmatic reticulum) of normal, i.e. not pretreated rats and of rats induced by aroclor 1254 (500 mg/kg) wer used. For the S-9 induced fraction, 3 different concentrations were tested.

Compound B was tested at concentrations of 0.25, 2.5, 5 and 10 mg/plate. In a prior serial dilution test the highest dosage used did not show an inhibition of the microorganism growth.

Compound B did not lead to an increase in the spontaneous mutation rate with any of the tested strains. No effect on enzyme induction and the activating fraction upon the reversion rate was detected. The colonies counted on the test plates showed the normal spontaneous range for each test strain.

The experiments showed that compound B does not induce base substitutions (*S. typhimurium* TA 1535, TA 100) or frame-shift mutations (*S. typhimurium* TA 1537, TA 1538, TA 98), thus indicating that the compound is not mutagenic.

For sweetening purposes the compounds of the present invention are incorporated into conventional sweetening compositions, that is, compositions consisting essentially of an inert carrier and an effectice sweetening amount of the sweetening agent, such as tablets, powders, solutions or the like.

The following examples illustrate a few sweetening compositions comprising a compound of the present invention as sweetening ingredient and represent the best modes contemplated of using the invention. The parts are parts by weight unless otherwise specified.

EXAMPLE 12

Solution

The solution is compounded from the following ingredients:

| | |
|---|---|
| Sorbic acid | 0.1 parts |
| Citric acid | 1.2 parts |
| Disodium phosphate | 1.5 parts |
| Sodium salt of 4-hydroxy-1,2-benzoisothiazol-3(2H)—one-1,1-dioxide | 5.0 parts |
| Distilled water | 100.0 parts by vol. |

Preparation:

The ingredients are successively dissolved in the distilled water at 60° C., while stirring. 1 ml of the solution (about 25 drops) contains 50 mgm of the sweetening ingredient and has a sweetening power which is equivalent to about three lumps of sugar.

EXAMPLE 13

Tablets

The tablet composition is compounded from the following ingredients:

| | |
|---|---|
| 4-Hydroxy-1,2-benzoisothiazol-3(2H)—one-1,1-dioxide | 20 parts |
| Sodium bicarbonate | 5 parts |
| Sorbitol, powdered | 25 parts |
| Total | 50 parts |

Preparation:

The ingredients are intimately admixed with each other, and the composition is compressed into 50 mgm-tablets at a maximum of 60% relative humidity. Each tablet contains 20 mgm of the sweetening ingredient and has a sweetening power which is equivalent to about one lump of sugar.

EXAMPLE 14

Tablets

The tablet composition is compounded from the following ingredients:

| | | |
|---|---|---|
| Sodium salt of 4,6-dihydroxy-1,2-benzoisothiazol-3(2H)—one-1,1-dioxide | | 20 parts |
| Sorbitol | | 30 parts |
| | Total | 50 parts |

Preparation:

The ingredients are intimately admixed with each other, and the composition is compressed into 50 mgm-tablets, each of which has a sweetening power which is equivalent to about one lump of sugar.

Any one of the other compounds embraced by formula I or a non-toxic, pharmacologically acceptable salt thereof may be substituted for the particular sweetening ingredient in Examples 12 through 14. Likewise, the amount of sweetening ingredient in these illustrative examples may be varied to achieve a higher or lower sweetening power, and the amounts and nature of the inert carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

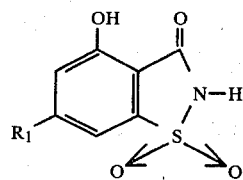

wherein $R_1$ is hydrogen or hydroxyl, or a non-toxic, pharmacologically acceptable salt thereof formed with an inorganic or organic base.

2. A compound of claim 1, which is 4-hydroxy-1,2-benzoisothiazol-3(2H)-one-1,1-dioxide or a non-toxic, pharmacologically acceptable salt thereof formed with an inorganic or organic base.

3. A compound of claim 1, which is 4,6-dihydroxy-1,2-benzoisothiazol-3(2H)-one-1,1-dioxide or a non-toxic, pharmacologically acceptable salt thereof formed with an inorganic or organic base.

4. A sweetening composition for foods and beverages, said composition consisting essentially of an inert carrier and an effective sweetening amount of a compound of claim 1.

5. The method of sweetening foods or beverages, which comprises adding thereto an effective sweetening amount of a compound of claim 1.

* * * * *